United States Patent
Racenet et al.

(10) Patent No.: US 8,061,577 B2
(45) Date of Patent: *Nov. 22, 2011

(54) TOOL ASSEMBLY FOR A SURGICAL STAPLING DEVICE

(75) Inventors: David C. Racenet, Litchfield, CT (US); Philip Roy, Orange, CT (US); John W. Beardsley, Wallingford, CT (US); Lee Ann Olson, Wallingford, CT (US); Ralph Stearns, Bozrah, CT (US); Clifford L. Emmons, Oakville, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/900,778

(22) Filed: Oct. 8, 2010

(65) Prior Publication Data

US 2011/0079628 A1    Apr. 7, 2011

Related U.S. Application Data

(63) Continuation of application No. 12/550,993, filed on Aug. 31, 2009, now Pat. No. 7,819,896, which is a continuation of application No. 12/128,004, filed on May 28, 2008, now Pat. No. 7,690,547, which is a continuation of application No. 11/998,037, filed on Nov. 28, 2007, which is a continuation of application No. 10/529,800, filed as application No. PCT/US03/031652 on Oct. 6, 2003, now Pat. No. 7,588,177.

(60) Provisional application No. 60/416,088, filed on Oct. 4, 2002.

(51) Int. Cl.
A61B 17/068    (2006.01)

(52) U.S. Cl. ............... 227/180.1; 227/175.1; 227/176.1; 227/181.1; 227/19; 606/219

(58) Field of Classification Search ............... 227/175.1, 227/176.1, 180.1, 181.1, 19; 606/219
See application file for complete search history.

(56) References Cited

U.S. PATENT DOCUMENTS

| | | | |
|---|---|---|---|
| 3,079,606 | A | 3/1963 | Bosbrov et al. |
| 3,490,675 | A | 1/1970 | Green et al. |
| 3,954,310 | A | 5/1976 | Rava |
| 4,322,624 | A | 3/1982 | Cornelissen |
| 4,370,004 | A | 1/1983 | Morikawa et al. |
| 4,429,695 | A | 2/1984 | Green |
| 4,473,077 | A | 9/1984 | Noiles et al. |
| 4,505,414 | A | 3/1985 | Filipi |
| 4,520,817 | A | 6/1985 | Green |

(Continued)

FOREIGN PATENT DOCUMENTS

DE    2744824    4/1978

(Continued)

OTHER PUBLICATIONS

European Search Report for EP 08003414.3-2310 date of completion Apr. 25, 2008.

(Continued)

*Primary Examiner* — Paul R. Durand
*Assistant Examiner* — Michelle Lopez

(57) ABSTRACT

A surgical stapling device including an independently rotatable tool assembly is disclosed. The tool assembly includes an anvil and a cartridge assembly which are movable in relation to each other between spaced and approximated positions.

13 Claims, 13 Drawing Sheets

U.S. PATENT DOCUMENTS

| | | | |
|---|---|---|---|
| 4,566,620 A | 1/1986 | Green et al. | |
| 4,589,413 A | 5/1986 | Malyshev et al. | |
| 4,602,634 A | 7/1986 | Barkley | |
| 4,608,981 A | 9/1986 | Rothfuss et al. | |
| 4,610,383 A | 9/1986 | Rothfuss et al. | |
| 4,620,752 A | 11/1986 | Fremerey et al. | |
| 4,633,861 A | 1/1987 | Chow et al. | |
| 4,633,874 A | 1/1987 | Chow et al. | |
| 4,671,445 A | 6/1987 | Barker et al. | |
| 4,703,887 A | 11/1987 | Clanton et al. | |
| 4,710,656 A | 12/1987 | Studer | |
| 4,728,020 A | 3/1988 | Green et al. | |
| 4,752,024 A | 6/1988 | Green et al. | |
| 4,784,137 A | 11/1988 | Kulik et al. | |
| 4,863,088 A | 9/1989 | Redmond et al. | |
| 4,892,244 A | 1/1990 | Fox et al. | |
| 4,978,049 A | 12/1990 | Green | |
| 4,991,764 A | 2/1991 | Mericle | |
| 5,040,715 A | 8/1991 | Green et al. | |
| 5,065,929 A | 11/1991 | Schulze et al. | |
| 5,074,454 A | 12/1991 | Peters | |
| 5,083,695 A | 1/1992 | Foslien et al. | |
| 5,084,057 A | 1/1992 | Green et al. | |
| 5,111,987 A | 5/1992 | Moeinzadeh et al. | |
| 5,129,570 A | 7/1992 | Schulze et al. | |
| 5,141,144 A | 8/1992 | Foslien et al. | |
| 5,170,925 A | 12/1992 | Madden et al. | |
| 5,246,156 A | 9/1993 | Rothfuss et al. | |
| RE34,519 E | 1/1994 | Fox et al. | |
| 5,282,807 A | 2/1994 | Knoepfler | |
| 5,307,976 A | 5/1994 | Olson et al. | |
| 5,312,023 A | 5/1994 | Green et al. | |
| 5,318,221 A | 6/1994 | Green et al. | |
| 5,326,013 A | 7/1994 | Green et al. | |
| 5,328,077 A | 7/1994 | Lou | |
| 5,332,142 A | 7/1994 | Robinson et al. | |
| 5,336,232 A | 8/1994 | Green et al. | |
| 5,358,506 A | 10/1994 | Green et al. | |
| 5,364,002 A | 11/1994 | Green et al. | |
| 5,364,003 A | 11/1994 | Williamson, IV | |
| 5,364,011 A | 11/1994 | Baker et al. | |
| 5,376,095 A | 12/1994 | Ortiz | |
| 5,381,943 A | 1/1995 | Allen et al. | |
| 5,382,255 A | 1/1995 | Castro et al. | |
| 5,383,880 A | 1/1995 | Hooven | |
| 5,395,033 A | 3/1995 | Byrne et al. | |
| 5,395,034 A | 3/1995 | Allen et al. | |
| 5,397,046 A | 3/1995 | Savage et al. | |
| 5,397,324 A | 3/1995 | Carroll et al. | |
| 5,407,293 A | 4/1995 | Crainich | |
| 5,413,268 A | 5/1995 | Green et al. | |
| 5,415,334 A | 5/1995 | Williamson, IV et al. | |
| 5,415,335 A | 5/1995 | Knodell, Jr. | |
| 5,417,361 A | 5/1995 | Williamson, IV | |
| 5,423,471 A | 6/1995 | Mastri et al. | |
| 5,425,745 A | 6/1995 | Green et al. | |
| 5,431,322 A | 7/1995 | Green et al. | |
| 5,431,323 A | 7/1995 | Smith et al. | |
| 5,433,721 A | 7/1995 | Hooven et al. | |
| 5,447,265 A | 9/1995 | Vidal et al. | |
| 5,452,837 A | 9/1995 | Williamson, IV et al. | |
| 5,456,401 A | 10/1995 | Green et al. | |
| 5,464,300 A | 11/1995 | Crainich | |
| 5,465,895 A | 11/1995 | Knodel et al. | |
| 5,467,911 A | 11/1995 | Tsuruta et al. | |
| 5,470,007 A | 11/1995 | Plyley et al. | |
| 5,470,010 A | 11/1995 | Rothfuss et al. | |
| 5,472,132 A | 12/1995 | Savage et al. | |
| 5,474,566 A | 12/1995 | Alesi et al. | |
| 5,476,206 A | 12/1995 | Green et al. | |
| 5,478,003 A | 12/1995 | Green et al. | |
| 5,480,089 A | 1/1996 | Blewett | |
| 5,482,197 A | 1/1996 | Green et al. | |
| 5,484,095 A | 1/1996 | Green et al. | |
| 5,484,451 A | 1/1996 | Akopov et al. | |
| 5,485,947 A | 1/1996 | Olson et al. | |
| 5,485,952 A | 1/1996 | Fontayne | |
| 5,487,499 A | 1/1996 | Sorrentino et al. | |
| 5,487,500 A | 1/1996 | Knodel et al. | |
| 5,489,058 A | 2/1996 | Plyley et al. | |
| 5,497,933 A | 3/1996 | DeFonzo et al. | |
| 5,505,363 A | 4/1996 | Green et al. | |
| 5,507,426 A | 4/1996 | Young et al. | |
| 5,518,163 A | 5/1996 | Hooven | |
| 5,518,164 A | 5/1996 | Hooven | |
| 5,529,235 A | 6/1996 | Boiarski et al. | |
| 5,531,744 A | 7/1996 | Nardella et al. | |
| 5,535,934 A | 7/1996 | Boiarski et al. | |
| 5,535,935 A | 7/1996 | Vidal et al. | |
| 5,535,937 A | 7/1996 | Boiarski et al. | |
| 5,540,375 A | 7/1996 | Bolanos et al. | |
| 5,551,622 A | 9/1996 | Yoon | |
| 5,553,765 A | 9/1996 | Knodel et al. | |
| 5,554,164 A | 9/1996 | Wilson et al. | |
| 5,554,169 A | 9/1996 | Green et al. | |
| 5,560,530 A | 10/1996 | Bolanos et al. | |
| 5,560,532 A | 10/1996 | DeFonzo et al. | |
| 5,562,239 A | 10/1996 | Boiarski et al. | |
| 5,562,241 A | 10/1996 | Knodel et al. | |
| 5,562,682 A | 10/1996 | Oberlin et al. | |
| 5,564,615 A | 10/1996 | Bishop et al. | |
| 5,571,116 A | 11/1996 | Bolanos et al. | |
| 5,573,543 A | 11/1996 | Akopov et al. | |
| 5,575,799 A | 11/1996 | Bolanos et al. | |
| 5,577,654 A | 11/1996 | Bishop | |
| 5,582,611 A | 12/1996 | Tsuruta et al. | |
| 5,584,425 A | 12/1996 | Savage et al. | |
| 5,586,711 A | 12/1996 | Plyley et al. | |
| 5,588,580 A | 12/1996 | Paul et al. | |
| 5,588,581 A | 12/1996 | Conlon et al. | |
| 5,597,107 A | 1/1997 | Knodel et al. | |
| 5,601,224 A | 2/1997 | Bishop et al. | |
| 5,607,095 A | 3/1997 | Smith et al. | |
| 5,624,452 A | 4/1997 | Yates | |
| 5,626,587 A | 5/1997 | Bishop et al. | |
| 5,628,446 A | 5/1997 | Geiste et al. | |
| 5,630,539 A | 5/1997 | Plyley et al. | |
| 5,630,540 A | 5/1997 | Blewett | |
| 5,630,541 A | 5/1997 | Williamson, IV et al. | |
| 5,632,432 A | 5/1997 | Schulze et al. | |
| 5,634,584 A | 6/1997 | Okorocha et al. | |
| 5,636,780 A | 6/1997 | Green et al. | |
| 5,645,209 A | 7/1997 | Green et al. | |
| 5,647,526 A | 7/1997 | Green et al. | |
| 5,653,371 A | 8/1997 | Green et al. | |
| 5,653,721 A | 8/1997 | Knodel et al. | |
| 5,655,698 A | 8/1997 | Yoon | |
| 5,657,921 A | 8/1997 | Young et al. | |
| 5,658,300 A | 8/1997 | Bito et al. | |
| 5,662,258 A | 9/1997 | Knodel et al. | |
| 5,662,259 A | 9/1997 | Yoon | |
| 5,662,260 A | 9/1997 | Yoon | |
| 5,662,662 A | 9/1997 | Bishop et al. | |
| 5,662,666 A | 9/1997 | Onuki et al. | |
| 5,667,517 A | 9/1997 | Hooven | |
| 5,669,544 A | 9/1997 | Schulze et al. | |
| 5,673,840 A | 10/1997 | Schulze et al. | |
| 5,673,841 A | 10/1997 | Schulze et al. | |
| 5,673,842 A | 10/1997 | Bittner et al. | |
| 5,676,674 A | 10/1997 | Bolanos et al. | |
| 5,680,981 A | 10/1997 | Mililli et al. | |
| 5,680,982 A | 10/1997 | Schulze et al. | |
| 5,690,269 A | 11/1997 | Bolanos et al. | |
| 5,692,668 A | 12/1997 | Schulze et al. | |
| 5,697,542 A | 12/1997 | Knodel et al. | |
| 5,704,534 A | 1/1998 | Huitema et al. | |
| 5,709,334 A | 1/1998 | Sorrentino et al. | |
| 5,711,472 A | 1/1998 | Bryan | |
| 5,713,505 A | 2/1998 | Huitema | |
| 5,716,366 A | 2/1998 | Yates | |
| 5,725,536 A | 3/1998 | Oberlin et al. | |
| 5,725,554 A | 3/1998 | Simon et al. | |
| 5,728,110 A | 3/1998 | Vidal et al. | |
| 5,735,848 A | 4/1998 | Yates et al. | |
| 5,743,456 A | 4/1998 | Jones et al. | |
| 5,749,893 A | 5/1998 | Vidal et al. | |
| 5,752,644 A | 5/1998 | Bolanos et al. | |

| | | | | | | |
|---|---|---|---|---|---|---|
| 5,762,255 | A | 6/1998 | Chrisman et al. | 6,786,382 B1 | 9/2004 | Hoffman |
| 5,762,256 | A | 6/1998 | Mastri et al. | 6,808,262 B2 | 10/2004 | Chapoy et al. |
| 5,769,303 | A | 6/1998 | Knodel et al. | 6,830,174 B2 | 12/2004 | Hillstead et al. |
| 5,772,673 | A | 6/1998 | Cuny et al. | 6,835,119 B2 | 12/2004 | Hori |
| 5,779,130 | A | 7/1998 | Alesi et al. | 6,835,199 B2 | 12/2004 | McGuckin et al. |
| 5,779,131 | A | 7/1998 | Knodel et al. | 6,843,403 B2 | 1/2005 | Whitman |
| 5,779,132 | A | 7/1998 | Knodel et al. | RE38,708 E | 3/2005 | Bolanos et al. |
| 5,782,396 | A | 7/1998 | Mastri et al. | 6,877,647 B2 | 4/2005 | Green et al. |
| 5,782,397 | A | 7/1998 | Koukline | 6,879,880 B2 | 4/2005 | Nowlin et al. |
| 5,782,834 | A | 7/1998 | Lucey et al. | 6,889,116 B2 | 5/2005 | Jinno |
| 5,797,536 | A | 8/1998 | Smith et al. | 6,905,057 B2 | 6/2005 | Swayze et al. |
| 5,797,537 | A | 8/1998 | Oberlin et al. | 6,986,451 B1 | 1/2006 | Mastri et al. |
| 5,797,538 | A | 8/1998 | Heaton et al. | 7,159,750 B2 | 1/2007 | Racenet et al. |
| 5,810,811 | A | 9/1998 | Yates et al. | 7,424,965 B2 | 9/2008 | Racenet et al. |
| 5,810,855 | A | 9/1998 | Rayburn et al. | 7,494,039 B2 | 2/2009 | Racenet et al. |
| 5,814,055 | A | 9/1998 | Knodel et al. | 2002/0004498 A1 | 1/2002 | Doherty |
| 5,816,471 | A | 10/1998 | Plyley et al. | 2002/0009193 A1 | 1/2002 | Deguchi |
| 5,817,109 | A | 10/1998 | McGarry et al. | 2002/0018323 A1 | 2/2002 | Li |
| 5,820,009 | A | 10/1998 | Melling et al. | 2002/0032948 A1 | 3/2002 | Ahn |
| 5,823,066 | A | 10/1998 | Huitema et al. | 2002/0036748 A1 | 3/2002 | Chapoy |
| 5,826,776 | A | 10/1998 | Schulze et al. | 2002/0045442 A1 | 4/2002 | Silen et al. |
| 5,829,662 | A | 11/1998 | Allen et al. | 2002/0069565 A1 | 6/2002 | Liao |
| 5,833,695 | A | 11/1998 | Yoon | 2002/0084304 A1 | 7/2002 | Whitman |
| 5,836,147 | A | 11/1998 | Schnipke | 2002/0111621 A1 | 8/2002 | Wallace |
| 5,862,972 | A | 1/1999 | Green et al. | 2002/0143346 A1 | 10/2002 | McGuckin |
| 5,865,361 | A | 2/1999 | Milliman et al. | 2002/0177843 A1 | 11/2002 | Anderson |
| 5,871,135 | A | 2/1999 | Williamson, IV et al. | 2002/0188294 A1 | 12/2002 | Couture |
| 5,873,873 | A | 2/1999 | Smith et al. | 2002/0190093 A1 | 12/2002 | Fenton |
| 5,897,562 | A | 4/1999 | Bolanos et al. | 2003/0009193 A1 | 1/2003 | Corsaro |
| 5,901,895 | A | 5/1999 | Heaton et al. | 2003/0105476 A1 | 6/2003 | Sancoff |
| 5,911,353 | A | 6/1999 | Bolanos et al. | 2003/0132268 A1 | 7/2003 | Whitman |
| 5,918,791 | A | 7/1999 | Sorrentino et al. | 2004/0004105 A1 | 1/2004 | Jankowski |
| 5,919,198 | A | 7/1999 | Graves, Jr. et al. | 2004/0007608 A1 | 1/2004 | Ehrenfels |
| 5,922,001 | A | 7/1999 | Yoon | 2004/0050902 A1 | 3/2004 | Green |
| 5,954,259 | A | 9/1999 | Viola et al. | 2004/0093029 A1 | 5/2004 | Zubik |
| 5,980,510 | A | 11/1999 | Tsonton et al. | 2004/0094597 A1 | 5/2004 | Whitman |
| 6,004,335 | A | 12/1999 | Vaitekunas et al. | 2004/0108357 A1 | 6/2004 | Milliman |
| 6,010,054 | A | 1/2000 | Johnson et al. | 2004/0149802 A1 | 8/2004 | Whitman |
| 6,032,849 | A | 3/2000 | Mastri et al. | 2004/0173659 A1 | 9/2004 | Green |
| 6,079,606 | A | 6/2000 | Milliman et al. | 2004/0199181 A1 | 10/2004 | Knodel |
| 6,109,500 | A | 8/2000 | Alli et al. | 2004/0232199 A1 | 11/2004 | Shelton |
| 6,119,913 | A | 9/2000 | Main et al. | 2004/0232200 A1 | 11/2004 | Shelton |
| 6,197,017 | B1 | 3/2001 | Brock et al. | 2004/0232201 A1 | 11/2004 | Wenchell |
| 6,202,914 | B1 | 3/2001 | Geiste et al. | 2004/0243151 A1 | 12/2004 | Demmy |
| 6,241,139 | B1 | 6/2001 | Milliman et al. | 2004/0267310 A1 | 12/2004 | Racenet |
| 6,250,532 | B1 | 6/2001 | Green et al. | 2005/0006429 A1 | 1/2005 | Wales |
| 6,264,086 | B1 | 7/2001 | McGuckin, Jr. | 2005/0006430 A1 | 1/2005 | Wales |
| 6,264,087 | B1 | 7/2001 | Whitman | 2005/0006431 A1 | 1/2005 | Shelton |
| 6,269,977 | B1 | 8/2001 | Moore | 2005/0006432 A1 | 1/2005 | Racenet |
| 6,279,809 | B1 | 8/2001 | Nicolo | 2005/0006433 A1 | 1/2005 | Milliman |
| 6,315,183 | B1 | 11/2001 | Piraka | 2005/0006434 A1 | 1/2005 | Wales |
| 6,315,184 | B1 | 11/2001 | Whitman | 2005/0023324 A1 | 2/2005 | Doll |
| 6,325,810 | B1 | 12/2001 | Hamilton et al. | 2005/0023325 A1 | 2/2005 | Gresham |
| 6,330,965 | B1 | 12/2001 | Milliman et al. | 2005/0067457 A1 | 3/2005 | Shelton |
| 6,436,097 | B1 | 8/2002 | Nardella | 2005/0067458 A1 | 3/2005 | Swayze |
| 6,439,446 | B1 | 8/2002 | Perry et al. | 2005/0067459 A1 | 3/2005 | Swayze et al. |
| 6,443,973 | B1 | 9/2002 | Whitman | 2005/0067460 A1 | 3/2005 | Milliman |
| 6,463,623 | B2 | 10/2002 | Ahn et al. | 2005/0072827 A1 | 4/2005 | Mullenauer |
| 6,488,196 | B1 | 12/2002 | Fenton, Jr. | 2005/0103819 A1 | 5/2005 | Racenet |
| 6,503,257 | B2 | 1/2003 | Grant et al. | 2005/0119669 A1 | 6/2005 | Demmy |
| 6,505,768 | B2 | 1/2003 | Whitman | 2005/0127131 A1 | 6/2005 | Mastri |
| 6,544,274 | B2 | 4/2003 | Danitz et al. | 2006/0011699 A1 | 1/2006 | Olson et al. |
| 6,554,844 | B2 | 4/2003 | Lee et al. | 2006/0016853 A1 | 1/2006 | Racenet |
| 6,565,554 | B1 | 5/2003 | Niemeyer | 2007/0034670 A1 | 2/2007 | Racenet et al. |
| 6,587,750 | B2 | 7/2003 | Gerbi et al. | 2007/0084897 A1 | 4/2007 | Shelton et al. |
| 6,592,597 | B2 | 7/2003 | Grant et al. | 2007/0108252 A1 | 5/2007 | Racenet et al. |
| 6,594,552 | B1 | 7/2003 | Nowlin et al. | 2008/0105730 A1* | 5/2008 | Racenet et al. ............ 227/176.1 |
| 6,602,252 | B2 | 8/2003 | Mollenauer | | | |
| 6,612,053 | B2 | 9/2003 | Liao | | | |
| 6,619,529 | B2 | 9/2003 | Green et al. | | | |
| 6,644,532 | B2 | 11/2003 | Green et al. | | | |
| 6,656,193 | B2 | 12/2003 | Grant et al. | | | |
| 6,669,073 | B2 | 12/2003 | Milliman et al. | | | |
| 6,698,643 | B2 | 3/2004 | Whitman | | | |
| 6,716,232 | B1 | 4/2004 | Vidal et al. | | | |
| 6,722,552 | B2 | 4/2004 | Fenton, Jr. | | | |
| 6,731,473 | B2 | 5/2004 | Li et al. | | | |
| 6,755,338 | B2 | 6/2004 | Hahnen et al. | | | |
| 6,783,524 | B2 | 8/2004 | Anderson et al. | | | |

FOREIGN PATENT DOCUMENTS

| | | |
|---|---|---|
| DE | 2903159 | 1/1980 |
| DE | 30 11 415 A1 | 10/1980 |
| DE | 34 09 047 A1 | 9/1985 |
| DE | 38 44 563 C2 | 11/1989 |
| DE | 4213426 | 10/1992 |
| DE | 4300307 | 7/1994 |
| DE | 44 36 831 C2 | 6/1995 |
| DE | 19951940 | 6/2001 |
| EP | 0041022 | 12/1981 |
| EP | 0136950 | 4/1985 |

| | | | | | | |
|---|---|---|---|---|---|---|
| EP | 0140552 | 5/1985 | | EP | 0640317 | 3/1995 |
| EP | 0156774 | 10/1985 | | EP | 0656188 | 6/1995 |
| EP | 0216532 | 4/1987 | | EP | 0365153 | 8/1995 |
| EP | 0220029 | 4/1987 | | EP | 0666057 | 8/1995 |
| EP | 0213817 | 11/1987 | | EP | 0705571 | 4/1996 |
| EP | 0273468 | 7/1988 | | EP | 0931512 | 7/1999 |
| EP | 0324166 | 7/1989 | | FR | 2542188 | 9/1984 |
| EP | 0324635 | 7/1989 | | FR | 2681775 | 10/1991 |
| EP | 0324637 | 7/1989 | | GB | 1352554 | 4/1971 |
| EP | 0324638 | 7/1989 | | GB | 1452185 | 10/1976 |
| EP | 0369324 | 5/1990 | | GB | 1555455 | 11/1979 |
| EP | 0373762 | 6/1990 | | GB | 2048685 | 12/1980 |
| EP | 0380025 | 8/1990 | | GB | 2070499 | 9/1981 |
| EP | 0399701 | 11/1990 | | GB | 2141066 | 12/1984 |
| EP | 0449394 | 10/1991 | | GB | 2165559 | 4/1986 |
| EP | 0484677 | 5/1992 | | JP | 59-200810 A | 11/1984 |
| EP | 0489436 | 6/1992 | | JP | 9-133133 A | 5/1997 |
| EP | 0503662 | 9/1992 | | RU | 980703 | 12/1982 |
| EP | 0514139 | 11/1992 | | RU | 990220 | 1/1983 |
| EP | 0536903 | 4/1993 | | SU | 728848 | 5/1977 |
| EP | 0537572 | 4/1993 | | SU | 659146 | 4/1979 |
| EP | 0539762 | 5/1993 | | WO | WO 89/10094 | 11/1989 |
| EP | 0545029 | 6/1993 | | WO | WO 9210976 | 7/1992 |
| EP | 0552050 | 7/1993 | | WO | WO 9308754 | 5/1993 |
| EP | 0552423 | 7/1993 | | WO | WO 8302247 | 7/1993 |
| EP | 0579038 | 1/1994 | | WO | WO 9314706 | 8/1993 |
| EP | 0589306 | 3/1994 | | WO | WO 2004/032754 A2 | 4/2004 |
| EP | 0591946 | 4/1994 | | | | |
| EP | 0592243 | 4/1994 | | | | |
| EP | 0593920 | 4/1994 | | | | |
| EP | 0598202 | 5/1994 | | | | |
| EP | 0598579 | 5/1994 | | | | |
| EP | 0621006 | 10/1994 | | | | |
| EP | 0621009 | 10/1994 | | | | |

OTHER PUBLICATIONS

Office Action issued in corresponding German Patent Application No. 102005030139.8 mailed on Mar. 16, 2005.

\* cited by examiner

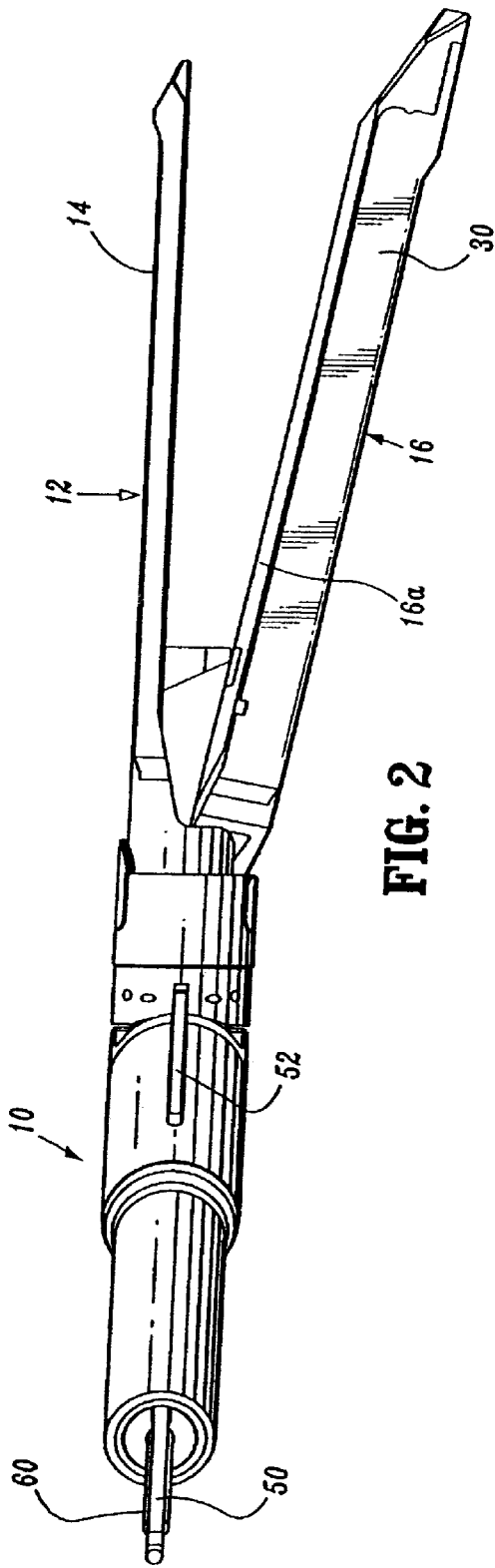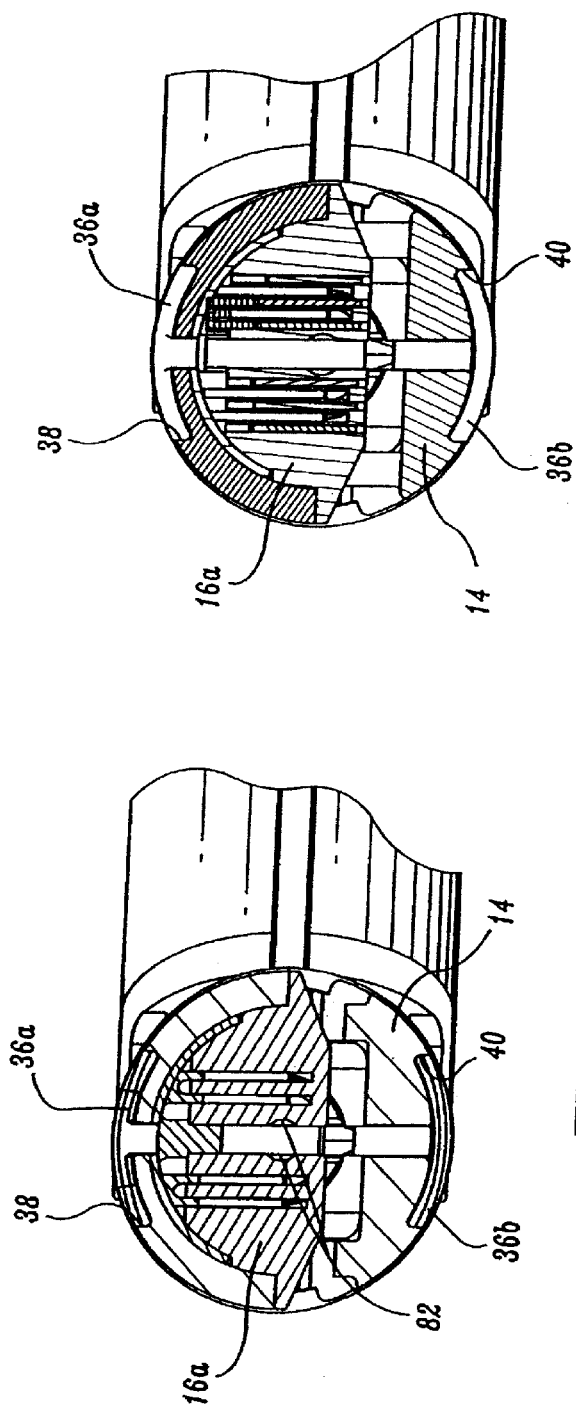

TOOL ASSEMBLY FOR A SURGICAL STAPLING DEVICE

CROSS-REFERENCE TO RELATED APPLICATIONS

This Application is a Continuation of U.S. application Ser. No. 12/550,993 filed Aug. 31, 2009, now U.S. Pat. No. 7,819,896, which is a Continuation of U.S. application Ser. No. 12/128,004 filed May 28, 2008, now U.S. Pat. No. 7,690,547, which is a Continuation of U.S. application Ser. No. 11/998,037 filed Nov. 28, 2007, which is a Continuation of U.S. application Ser. No. 10/529,800 filed Mar. 30, 2005, now U.S. Pat. No. 7,588,177, which is a National Stage Application of PCT/US03/31652 under 35 U.S.C. §371(a), filed Oct. 6, 2003, which claims priority from U.S. Provisional Application Ser. No. 60/416,088 filed Oct. 4, 2002, and the disclosures of each of the above-identified Applications are hereby incorporated by reference in their entirety.

BACKGROUND

1. Technical Field

The present disclosure relates to a tool assembly for treating tissue. More particularly, the present disclosure relates to an endoscopic surgical tool assembly capable of articulation and rotation for treating tissue.

2. Background of Related Art

Surgical staplers for clamping tissue between opposed jaw structures of a tool assembly and thereafter fastening the clamped tissue are well known in the art. These devices may include a knife for incising the fastened tissue. Such staplers having laparoscopic or endoscopic configurations are also well known in the art. Examples of these endoscopic surgical staplers are described in U.S. Pat. Nos. 6,330,965, 6,250,532, 6,241,139, 6,109,500 and 6,079,606, all of which are incorporated herein by reference in their entirety.

Typically, these staplers include a tool member having a staple cartridge for housing a plurality of staples arranged in at least two laterally spaced rows and an anvil which includes a plurality of staple forming pockets for receiving and forming staple legs of the staples as the staples are driven from the cartridge. The anvil, typically, is pivotally supported adjacent the cartridge and is pivotable between open and closed positions.

During laparoscopic or endoscopic surgical procedures, access to a surgical site is achieved through a small incision or through a narrow cannula inserted through a small entrance wound in a patient. Because of limited area to access the surgical site, many endoscopic staplers include mechanisms for rotating the endoscopic body portion of the device or articulating the tool assembly of the device. Typically, each mechanism is controlled by an actuator which has to be manipulated by a surgeon to properly orient the tool assembly in relation to tissue to be treated. Such manipulations are time consuming and may not result in the exact orientation of the tool assembly desired by the surgeon.

Accordingly, a need exists for an improved endoscopic surgical stapling device which includes a mechanism for adjusting the orientation of a tool assembly which is easy to operate and is capable of positioning a tool assembly at any desired orientation.

SUMMARY

In accordance with the present disclosure, a surgical instrument including a tool assembly having a pair of jaws is disclosed. The tool assembly includes an anvil and a cartridge assembly which has a plurality of fasteners supported therein. The cartridge assembly is movable in relation to the anvil between a spaced position and an approximated position. A clamp member is movable from a retracted position to an advanced position to move the cartridge assembly in relation to the anvil from the spaced position to the approximated position. A dynamic clamping member is movably positioned in relation to the anvil and cartridge assembly from a retracted to an advanced position to eject the plurality of fasteners from the cartridge assembly. A drive member formed from a flexible cable is operably connected to the clamp member and the dynamic clamping member and is movable to move the clamp member and the dynamic clamping member between their retracted and advanced positions.

Preferably, the drive member includes a coaxial cable including an outer sheath and a center rod. The center rod is axially movable and rotatable in relation to the outer sheath. The outer sheath is operably connected to the clamp member and the center rod is operably connected to the closure member.

Preferably, a collar is pivotally secured to a body portion of a stapling device. The body portion may form the distal end of a surgical stapling device or the proximal end of a disposable loading unit.

Preferably, the tool assembly is rotatably mounted to the collar member. In a preferred embodiment, the center rod of the coaxial cable is connected to the dynamic clamping device such that rotation of the center rod effects rotation of the closure member to effect rotation of the tool assembly in relation to the collar member to facilitate independent rotation of the tool assembly.

In a preferred embodiment, the dynamic clamping member includes a first flange portion positioned to engage a surface of the anvil and a second flange portion positioned to engage a surface of the cartridge assembly. The first and second flange portions together define a maximum tissue gap between the anvil and cartridge assembly.

BRIEF DESCRIPTION OF THE DRAWINGS

Various preferred embodiments of the presently disclosed surgical stapling device are disclosed herein with reference to the drawings, wherein:

FIG. 2 is a side view of the surgical stapling device shown in FIG. 1;

FIG. 5 is a cross-sectional view of the surgical stapling device shown in FIG. 3 taken along a transverse axis through the dynamic clamping member with the tool member approximated;

FIG. 6 is a cross-sectional view of the surgical stapling device shown in FIG. 3 taken along a transverse axis of the tool assembly through the cartridge assembly and anvil;

DETAILED DESCRIPTION OF PREFERRED EMBODIMENTS

Figure 1:
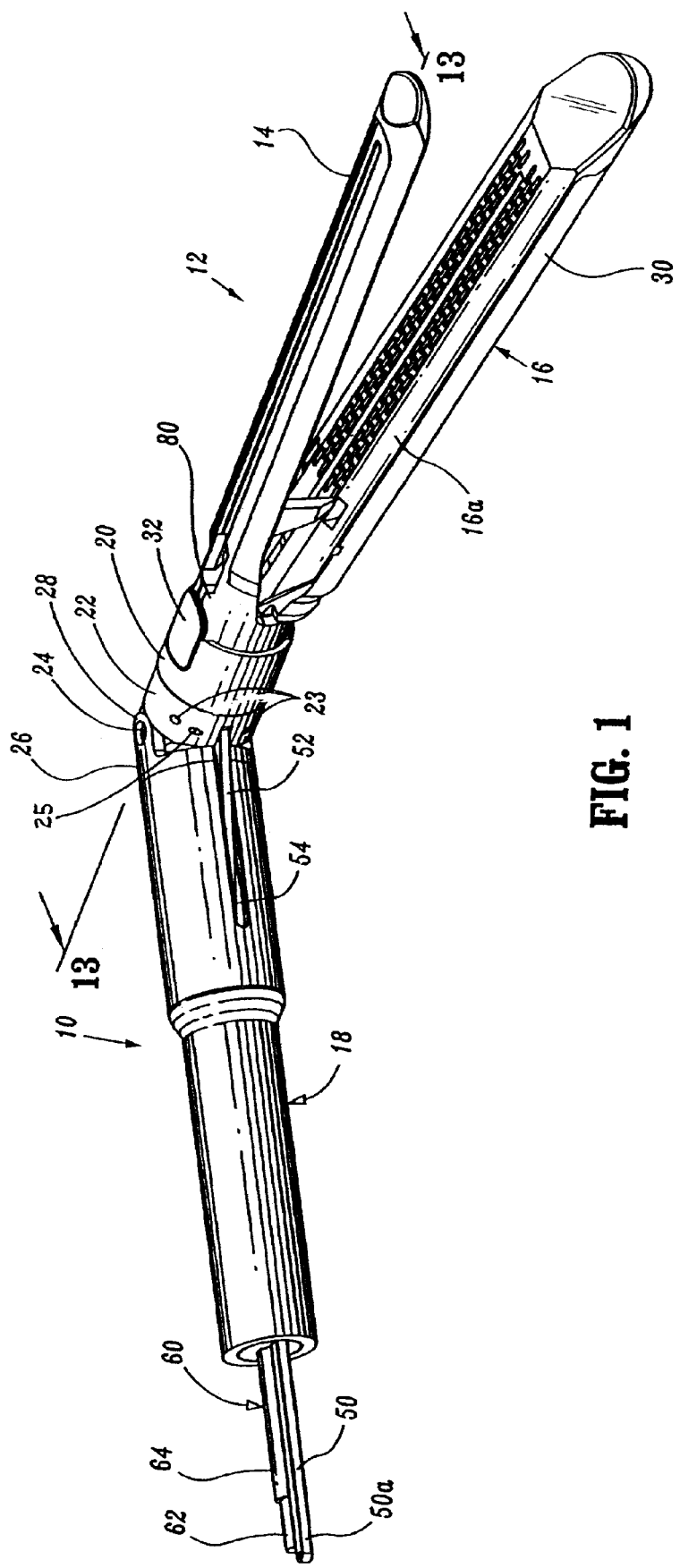
FIG. 1 is a side perspective view of one preferred embodiment of the presently disclosed surgical stapling device with the anvil and cartridge assembly in the spaced position.

Preferred embodiments of the presently disclosed surgical stapling device will now be described in detail with reference to the drawings in which like reference numerals designate identical or corresponding elements in each of the several views.

Figure 12:
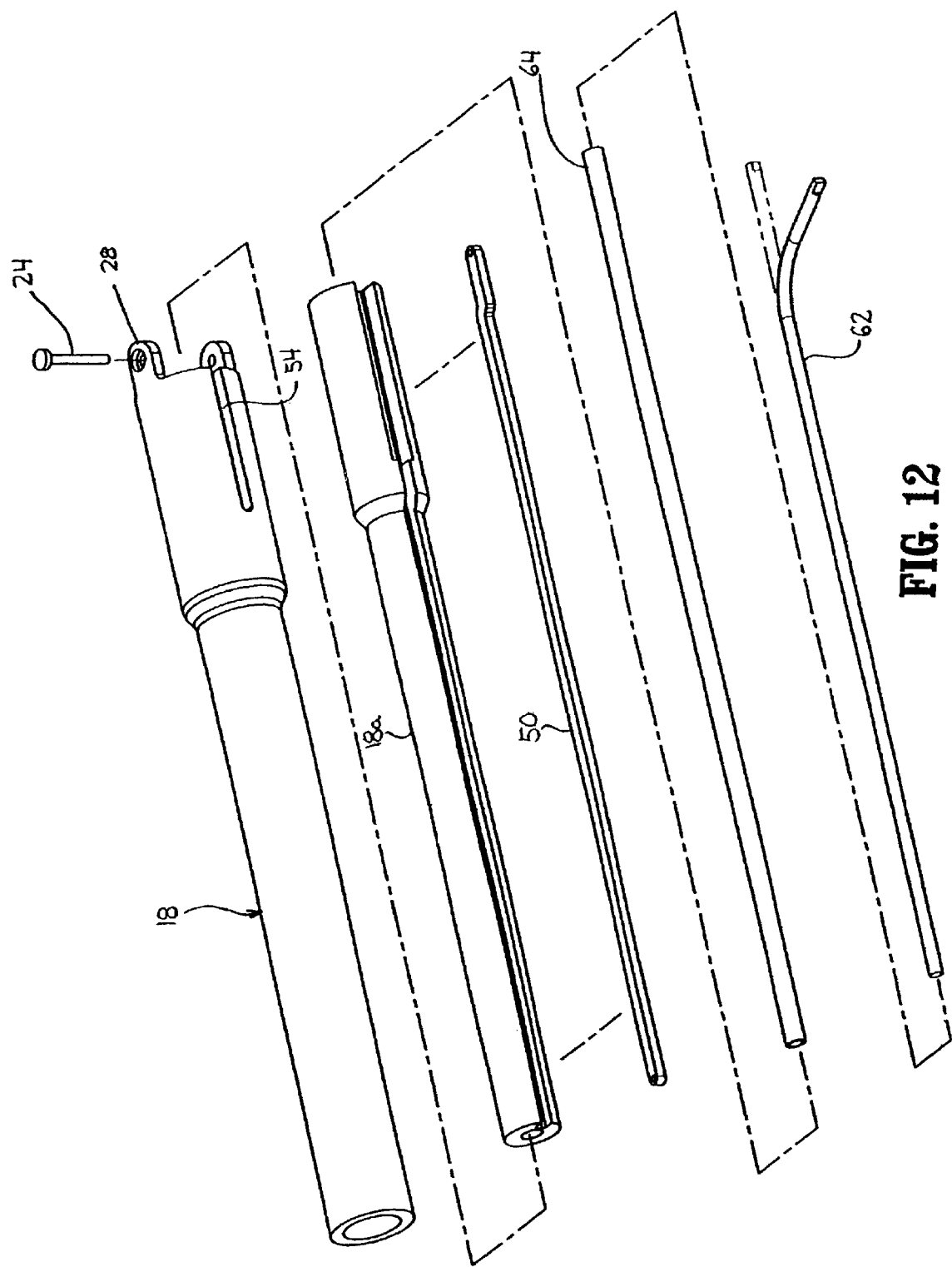
FIG. 12 is a side perspective exploded view of the endoscopic body portion of the surgical stapling device shown in FIG. 1.

FIGS. 1-13 illustrate one preferred embodiment of the presently disclosed surgical stapling device shown generally as 10. Stapling device 10 includes a tool assembly 12 having an anvil 14 and a cartridge assembly 16, an endoscopic body portion 18, a clamp member 20, and a rotation collar 22. Tool assembly 12 is pivotally supported at the distal end of endoscopic body portion 18 about a pivot member 24. An adaptor 26 is secured to the distal end of body portion 18 and includes upper and lower extensions 28. A spacer 18a (FIG. 12) may be positioned within body anterior 8 to maintain the positioning of the internal components of the device. Alternately, adaptor 26 can be monolithically formed with endoscopic body portion 18. Pivot member 24 extends between upper and lower extensions 28 and a proximal portion 22a (FIG. 1A) of rotation collar 22 such that tool assembly 12 can articulate in relation to the longitudinal axis of endoscopic portion 18 approximately 90°. It is envisioned that a variety of different articulation joint types, e.g, ball and socket, flexible coupling, universal joint etc., may be provided to allow for greater degrees of articulation.

Figure 7:
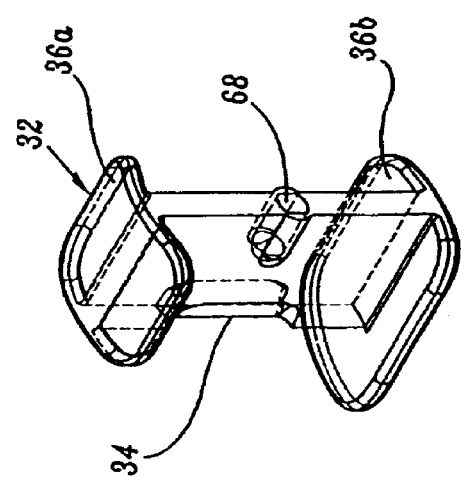
FIG. 7 is a top perspective view of the dynamic clamping member of the surgical stapling device shown in FIG. 1.
Figure 10:
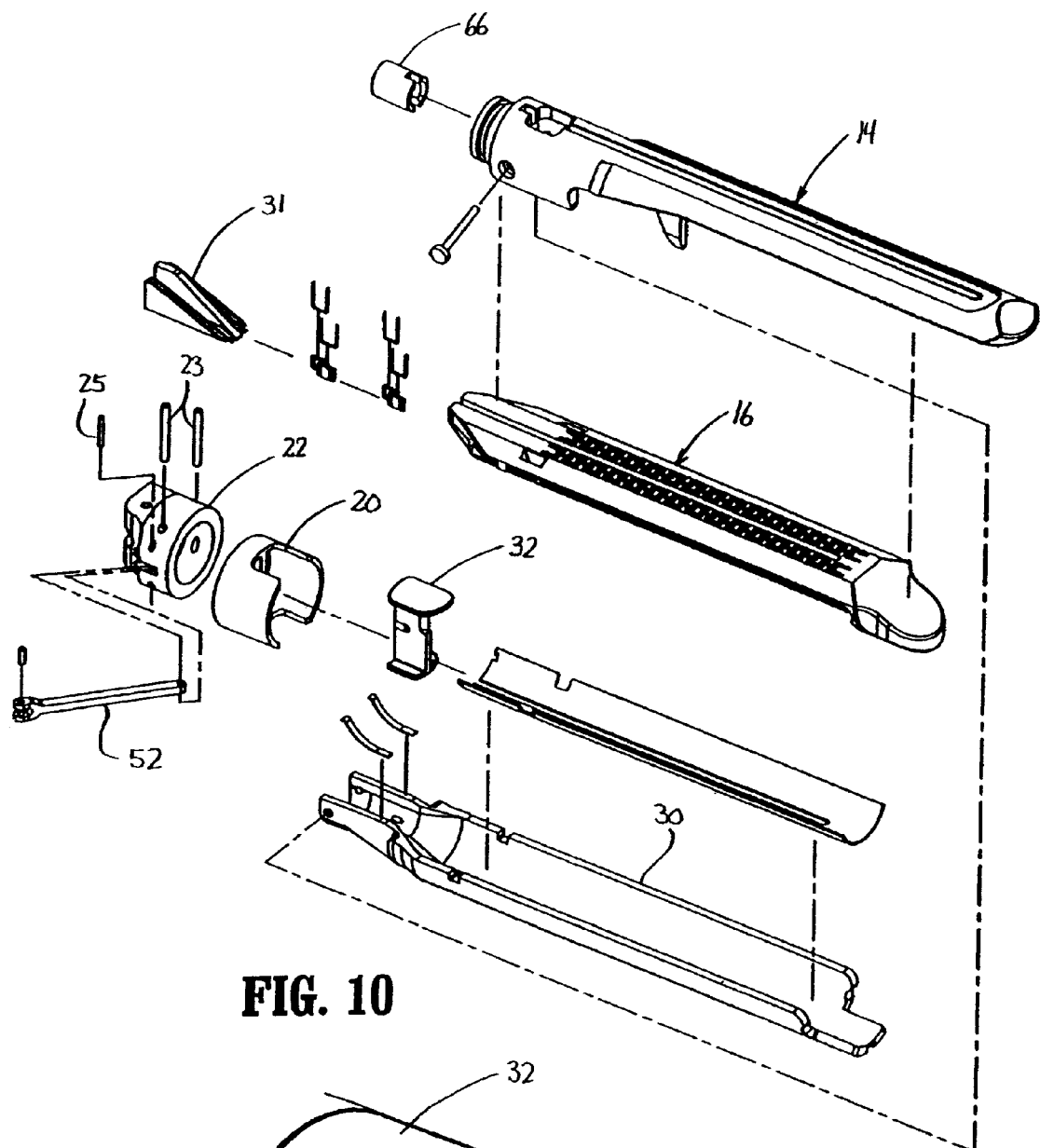
FIG. 10 is a side perspective exploded view of the tool assembly of the surgical stapling device shown in FIG. 1.
Figure 11:
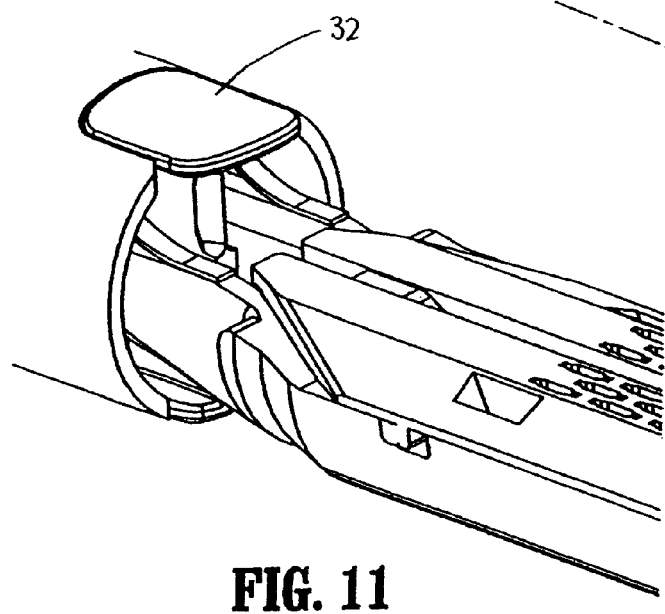
FIG. 11 is an enlarged view of the proximal end of the tool assembly shown in FIG. 10.

Cartridge assembly 16 includes a cartridge 16a housing a plurality of staples (not shown), a channel portion 30 defining a recess for receiving cartridge 16a, a dynamic clamping member 32 (FIG. 7), and a sled 31. Dynamic clamping member 32 preferably is positioned proximally of the sled 31 within cartridge 16a. A knife blade 34 is preferably positioned on an intermediate, preferably central, body portion 32a of dynamic clamping member 32 to incise fastened tissue. The knife blade 34 may be machined directly into the dynamic clamping member or may be fixedly or removably secured thereto. Alternately, knife blade 34 may be formed on or fixedly, removably or pivotally secured to the sled. Sled 31 is slidably positioned to translate through cartridge 16a to eject staples from the cartridge in a known manner. Dynamic clamping member 32 includes upper and lower flanges 36a and 36b. As shown in FIG. 5, flange 36a is positioned within a slot or recess 38 formed in cartridge 16a and flange 36b is positioned within a recess 40 formed in anvil 14. Alternately, flanges 36a and 36b need not be slidably positioned in recesses but rather need only engage an upper bearing surface on anvil 14 and a lower bearing surface on cartridge assembly 16. As illustrated in FIG. 7, flanges 36a and 36b preferably are arcuate or semi-circular to minimize deflection and maintain alignment of the anvil and/or cartridge during actuation of the stapler. Dynamic clamping member 32 is positioned proximally of the sled in engagement therewith and is translatable through the cartridge. Closure member 32 provides, restores and/or maintains a desired, preferably uniform, tissue gap in the area of tool assembly 12 adjacent sled 31 during firing of device 10. Movement of dynamic clamping member 32 through cartridge assembly 16 advances the sled through the cartridge assembly.

It is envisioned that the anvil and/or dynamic clamping member, preferably both, be formed of a material and be of such a thickness or gauge to minimize deflection of the respective anvil and/or dynamic clamping member during clamping, translation through, and firing of the device. Such materials include surgical grade stainless steel. Preferably, the anvil is formed as a solid one piece unit. Alternately, as known in the art, the anvil may be formed of an assembly of parts including an anvil body and anvil plate having a plurality of staple forming pockets. It is desired that the anvil be as strong as reasonably possible and necessary to minimize distortion, e.g., the distal end of the anvil bowing upwardly during clamping or preclamping and/or during staple firing.

Figure 1A:
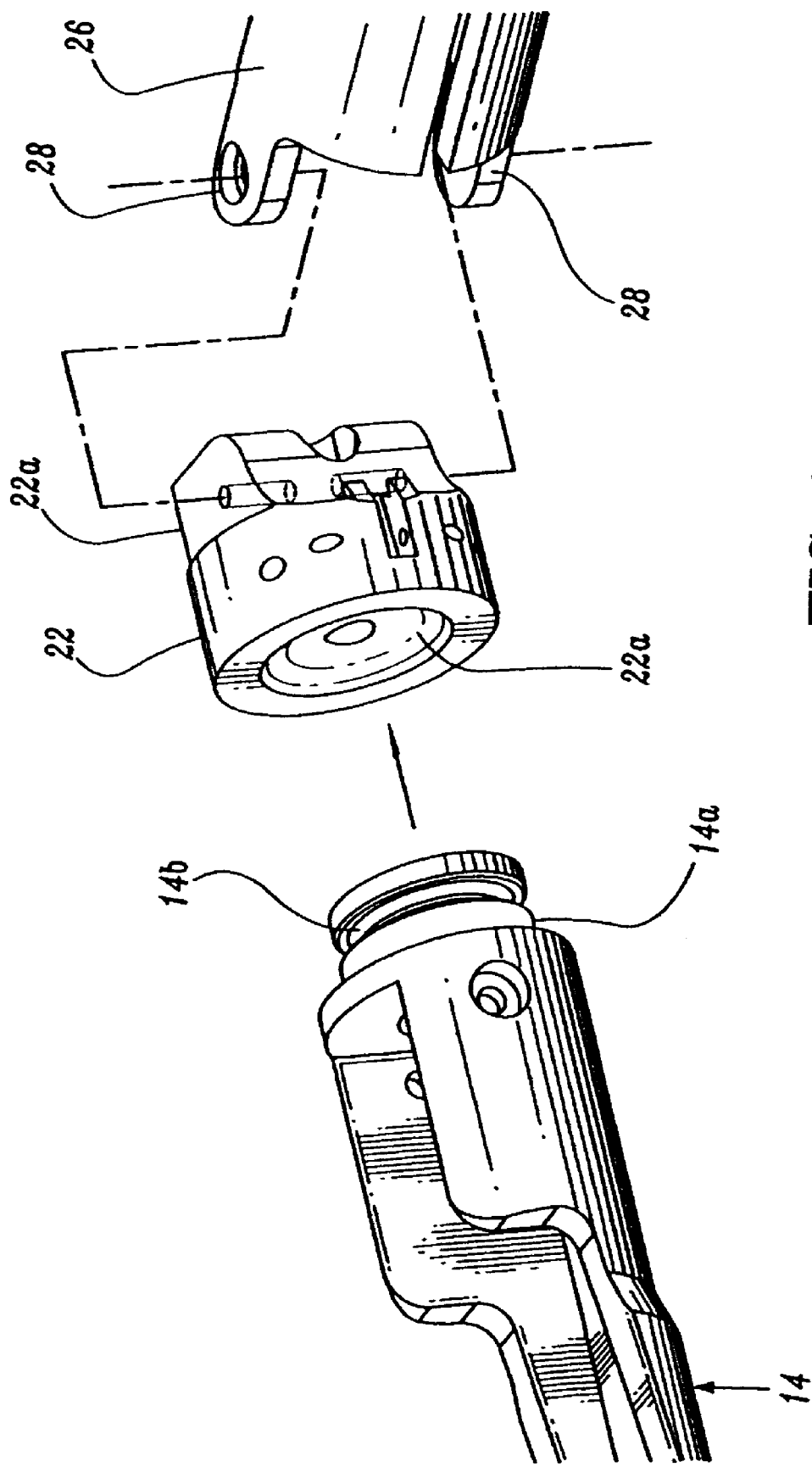
FIG. 1A is a side perspective view of the proximal end of the anvil, the rotation collar and the adaptor of the surgical stapling device shown in FIG. 1.
Figure 3:
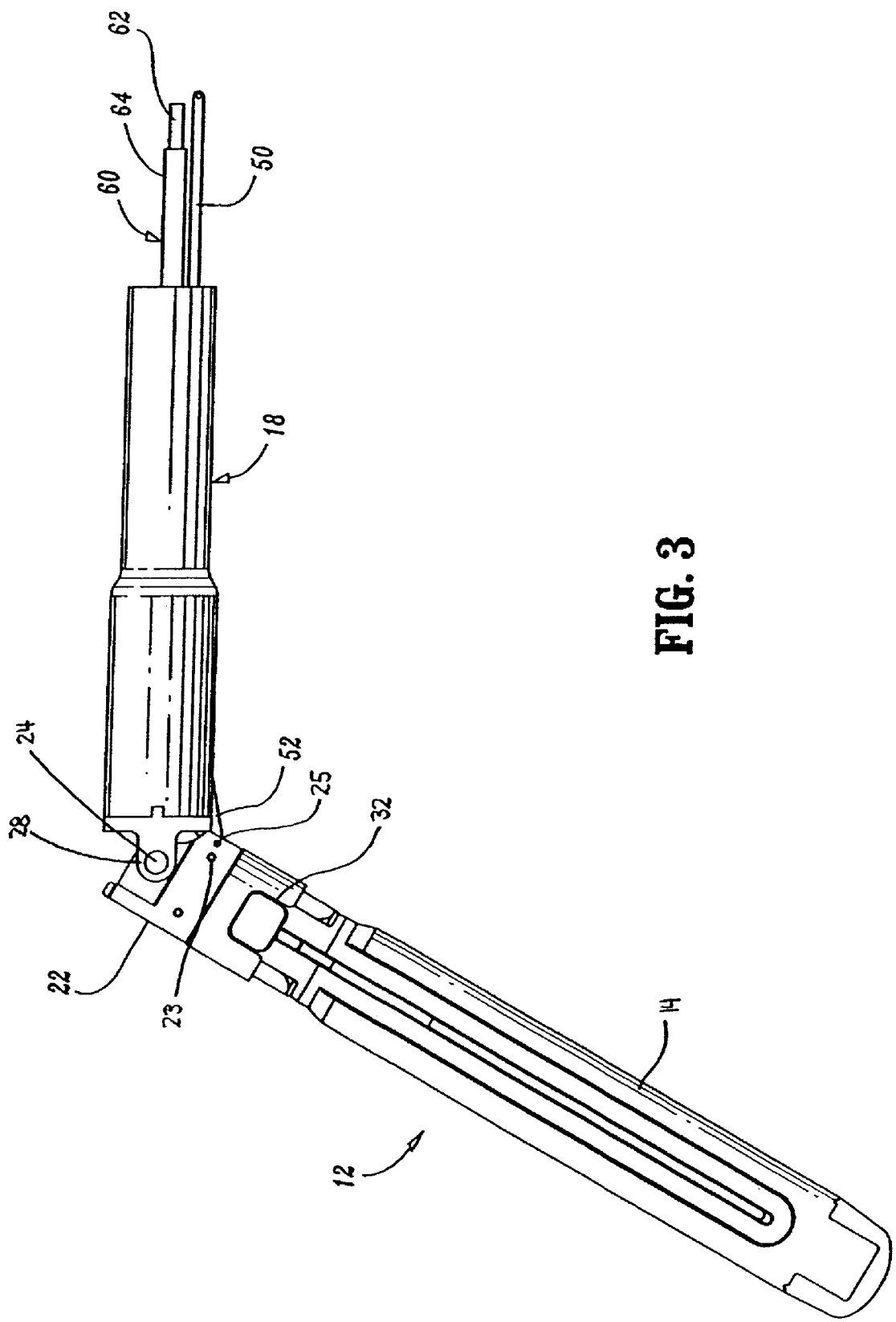
FIG. 3 is a top view with the internal components in phantom of the surgical stapling device shown in FIG. 2.

Referring to FIG. 1A, the proximal end of anvil 14 includes a cylindrical portion 14a having an annular recess 14b. Cylindrical portion 14a is dimensioned to be received within bore 22a of collar 22. At least one pivot pin 23 (FIG. 1) extends through collar 22 into recess 14b to axially fix the proximal end of anvil 14 within bore 22a. Since pin 23 is positioned within annular recess 14b, anvil 14 is rotatable within collar 22. It is envisioned that other means may be provided to rotatably attach anvil 14 to collar 22. A second pin 25 (FIG. 1) extends through collar 22 to secure collar 22 to a distal end of articulation link 52 as will be described below.

Although not shown, in a known manner the proximal end of channel portion 30 of cartridge assembly 16 includes a recess for receiving a pivot member, e.g., a tab or pin, formed on or attached to the proximal end of anvil 14. The proximal ends of anvil 14 and cartridge 16 are confined within collar 22 to prevent the pivot member of the anvil from becoming disengaged from the recess in channel portion 30 of cartridge assembly 16. Alternately, other mechanical arrangements known in the art may be used to pivotally secure anvil 14 to cartridge assembly 16. It is noted that since cartridge assembly 16 is pivotably attached to anvil 14, both are rotatable in relation to collar 22.

Figure 4:
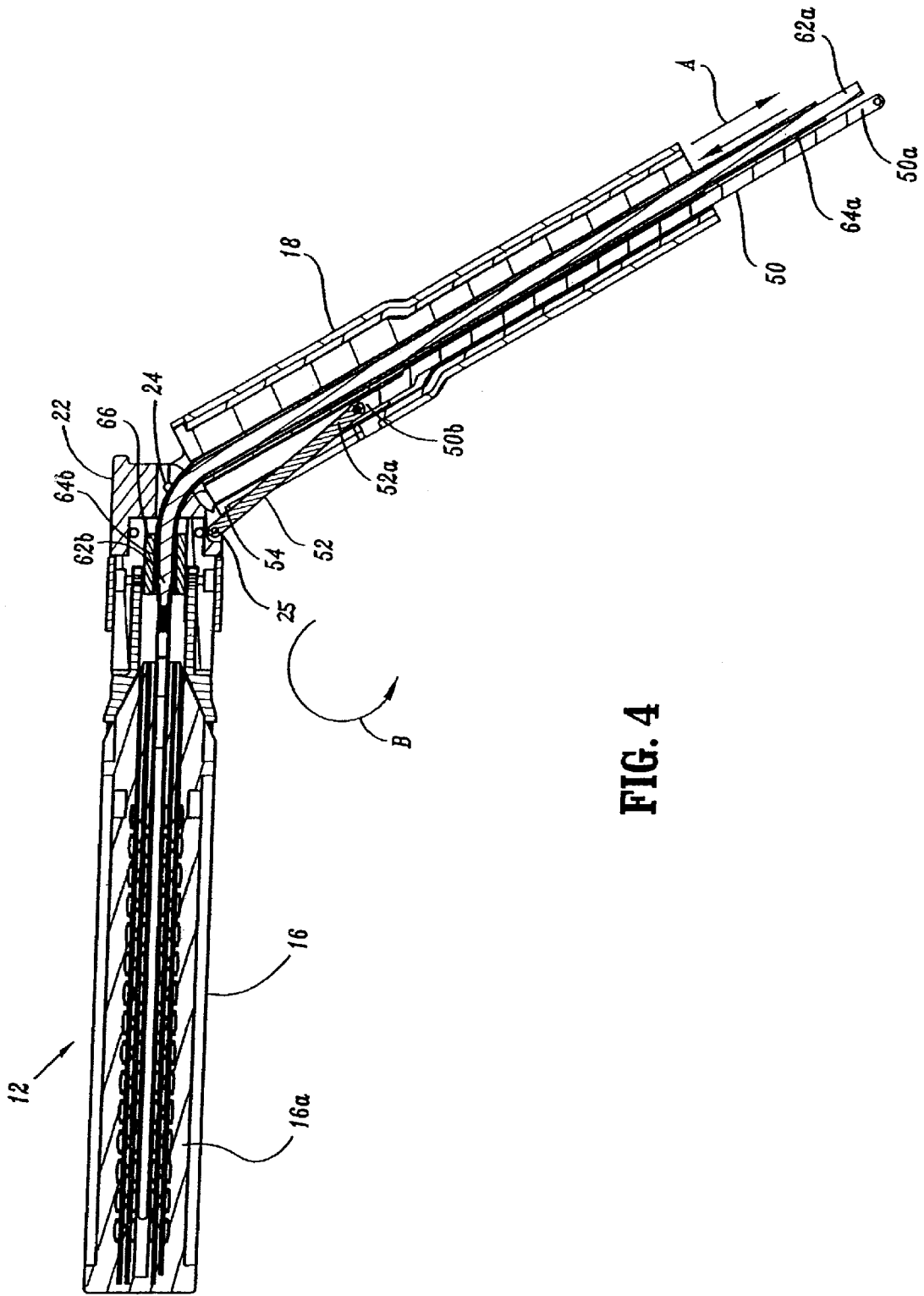
FIG. 4 is a cross-sectional view of the surgical stapling device shown in FIG. 2 taken along a longitudinal axis of the device through the cartridge assembly.
Figure 9:
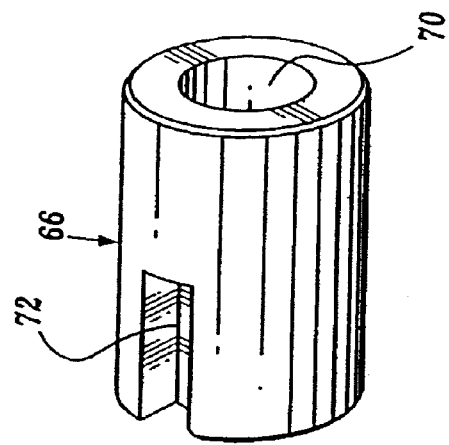
FIG. 9 is a top perspective view of the drive collar of the surgical stapling device shown in FIG. 1.
Figure 8:
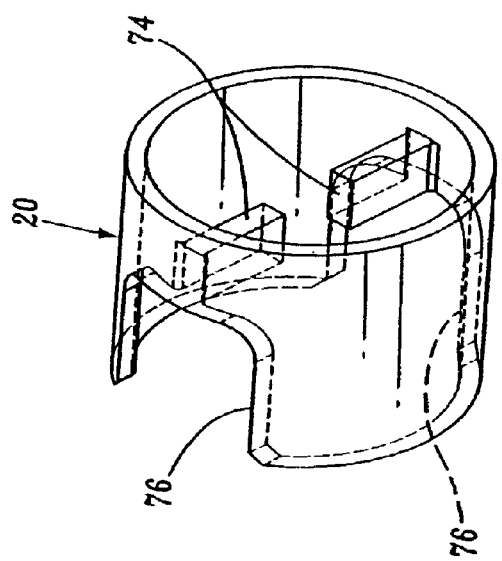
FIG. 8 is a top perspective view of the clamp member of the surgical stapling device shown in FIG. 1.

Referring to FIGS. 1 and 4, an articulation mechanism is provided to articulate tool assembly 12 in relation to endoscopic body portion 18. The articulation mechanism includes a proximal articulation link 50 and a distal articulation link 52. Proximal articulation link 50 has a first end 50a extending from the proximal end of endoscopic body portion 18 and a second end 50b positioned within body portion 18 and pivotally connected to a first end 52a of second articulation link 52. A second end 52b of articulation link 52 is pivotally connected to rotation collar 22 by pin 25 (FIG. 1) at a point offset from pivot member 24, i.e., the pivot axis of tool assembly 12. Articulation link 52 is confined in a slot 54 formed in endoscopic body portion 18. Because of the confinement, the articulation mechanism is only capable of articulating tool assembly 12 over an arc on one side of the longitudinal axis of the device. Preferably, each of the pivotal connections identified above includes a pivot pin. Alternately, pivot members may be integrally formed with the above components or pivot members not including pins may be used. Other types of articulation links are also contemplated.

In use, when the longitudinal axis of tool assembly 12 is aligned with the longitudinal axis of body portion 18 and proximal articulation link 50 is retracted in the direction indicated by arrow "A" in FIG. 4, link 50 retracts link 52 to effect articulation of tool assembly 12 about pivot member 24 in the direction indicated by arrow "B" in FIG. 4. Tool assembly 12 can be returned to a non-articulated position by advancing link 50 in the direction indicated by arrow "C". The mechanism for controlling movement of articulation mechanism will be discussed below.

Referring to FIGS. 3-9, a drive mechanism for approximating anvil 14 and cartridge assembly 16, firing the staples, and rotating tool assembly 12 in relation to collar 22 is provided. The drive mechanism includes a coaxial cable or drive member 60 (FIG. 3) having a center rod 62 and an outer sheath 64, a drive collar 66 (FIG. 9), a clamp member, here shown as a clamp ring 20, and dynamic clamping member 32. Center rod 62 is or includes a flexible member having a suitable compression strength for pushing dynamic clamping member 32 through cartridge 16a. Preferably, center rod 62 includes a left or right hand wound flexible cable. Alternately, other materials having suitable strength characteristics may also be used, e.g., Nitinol™. The diameter of center rod 62 must be small enough to be positioned within available space within cartridge 16a. Outer sheath 64 is positioned about center rod 62 and in part functions to stabilize and prevent buckling of center rod 62 while it is in compression. Preferably, outer sheath 62 is also a flexible cable formed from a steel mesh, reinforced plastic or a nickel titanium alloy such as Nitinol™. It is also envisioned that other suitable materials having the requisite strength requirements including a poly para-phenyleneterephthalamide material such as Kevlar™ commercially available from DuPont, may be used to form the outer sheath.

Center rod 62 is slidably positioned within outer sheath 64 and includes a first proximal end 62a (FIG. 4) preferably extending from the proximal end of endoscopic body portion 18 and a second end 62b attached to dynamic clamping member 32. Dynamic clamping member 32 preferably includes a recess 68 (FIG. 7) formed therein for receiving second end 62b of center rod 62. Second end 62b can be secured to dynamic clamping member 32 by crimping, welding as in FIG. 4, brazing, pins, etc. within or utilizing for example recess 68 and, may also be machined to conform to the shape of recess 68.

Outer sheath 64 has a first proximal end 64a extending preferably from the proximal end of elongated body portion 18 and a second distal end 64b fixedly connected to drive collar 66. Drive collar 66 (FIG. 9) preferably includes a central bore 70 for receiving outer sheath 64 and providing a channel for passage of center rod 62 therethrough. The outer surface of drive collar 66 preferably includes engagement structure, e.g., notches 72, for engaging clamp member or ring 20 in a rotatably fixed relation. Clamp ring 20 also includes engagement structure, e.g., veins or projections 74, for mating with the engagement structure of drive collar 66 to rotatably secure drive collar 66 to clamp ring 20 so that they will rotate together. The distal end 20a of clamp ring 20 includes a pair of cutouts 76 configured to receive and engage flange portions 36a and 36b of dynamic clamping member 32.

In use, center rod 62 and outer sheath 64 are movable together from a retracted position to a partially advanced position to advance drive collar 66, clamp ring 20 and dynamic clamping member 32 to a first advanced position. Clamp ring 20, preferably, is positioned about the proximal end of anvil 14 and cartridge assembly 16. Cartridge assembly 16 includes a cam surface 80 (FIG. 2) formed on an external surface thereof. As dynamic clamping member 32 moves from the retracted position to the first advanced position, flange 36b of dynamic clamping member 32 engages cam surface 80 of cartridge assembly 16 to pivot cartridge assembly 16 from the open position to the closed or clamped position. Clamp ring 20 is also moved distally from the first advanced position to a position encircling the proximal portions of anvil 14 and cartridge assembly 16. In this position, clamp ring 20 prevents the gap between proximal portions of anvil 14 and cartridge assembly 16 from exceeding a predetermined distance.

After center rod 62 and outer sheath 64 have been moved to the first advanced position to move cartridge assembly 16 and, accordingly, anvil 14 to the clamped position, center rod 62 can be advanced independently of outer sheath 64 to a second advanced position to move dynamic clamping member 32 through cartridge 16a to eject staples from the cartridge assembly and cut tissue by use of knife blade 34 of closure member 32. It is contemplated that, alternately, flanges 36a and 36b of closure member 32 could engage a cam surface on anvil 14 and/or cartridge assembly 16 to pivot one or both to provide clamping of tissue. Referring to FIGS. 5 and 6, a channel 82 is formed in cartridge 16a to provide lateral support to center rod 62 to prevent center rod 62 from buckling during movement of center rod 62 from the retracted position to the second advanced position.

As discussed above, anvil 14 is rotatably secured to collar 22, center rod 62 is fixedly attached to dynamic clamping member 32, and outer sheath 64 is fixedly attached to drive collar 66. When coaxial member 60 is rotated, the entire tool assembly rotates about the central axis of collar 22. More specifically, since dynamic clamping member 32 is confined within anvil 14 and cartridge assembly 16, any torque applied to center rod 62 is transferred via dynamic clamping member 32 to tool assembly 12. Thus coaxial member 60 can be rotated to rotate tool assembly 12 about the longitudinal axis of collar 22.

Figure 13:
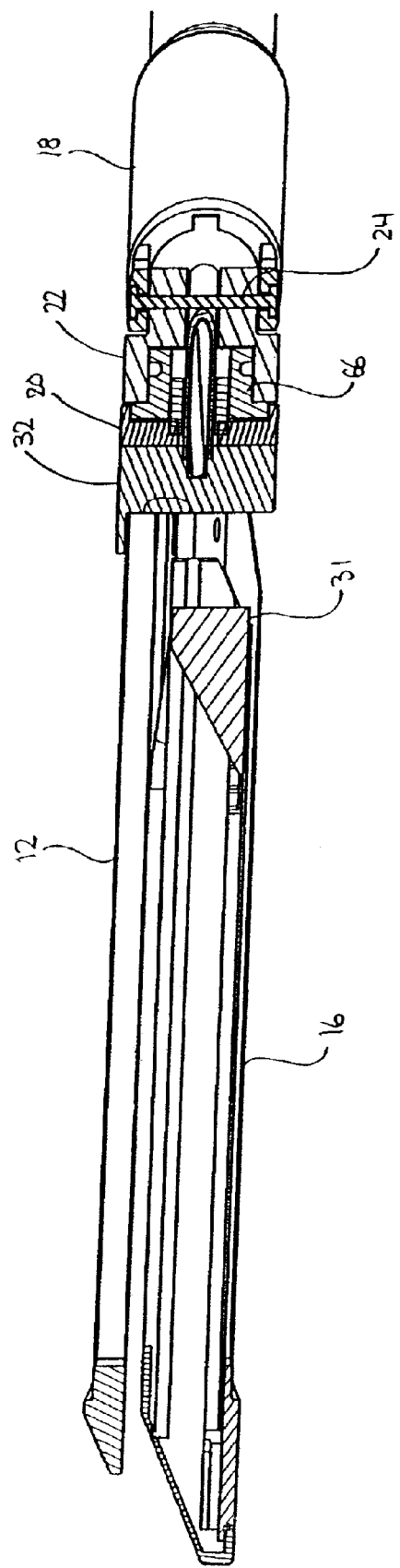
FIG. 13 is a side cross-sectional view of the surgical stapling device shown in FIG. 1.
Figure 13A:
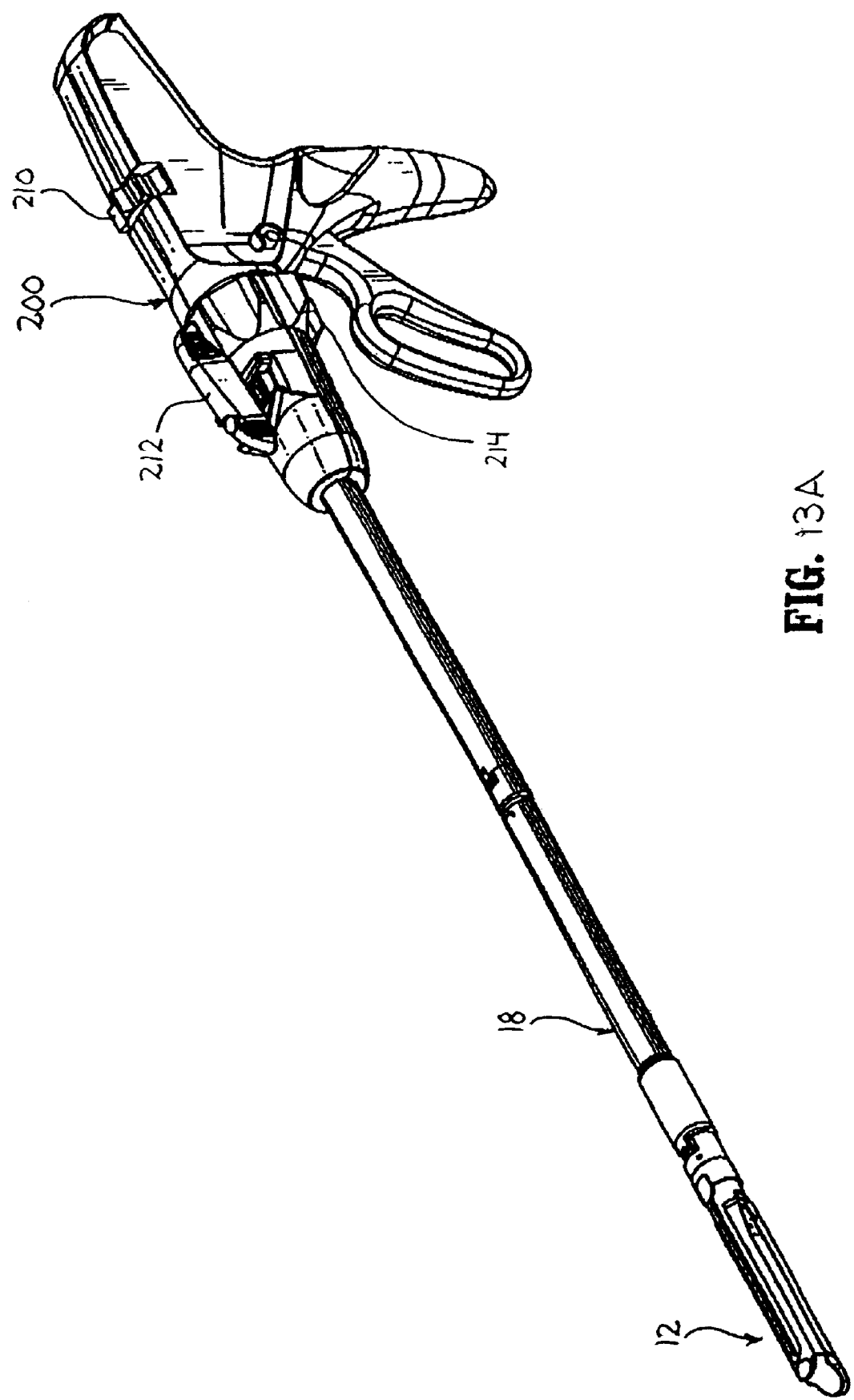

The above-described tool assembly may be, modified to be, or may be incorporated into a disposable loading unit such as disclosed in U.S. Pat. No. 6,330,965 or attached directly to the distal end of any known surgical stapling device. Although a handle assembly for actuating the articulation member and the approximation or clamping, firing, and tool rotation mechanisms have not been specifically disclosed herein, it is to be understood that the use of a broad variety of different actuating mechanisms and handle configurations are envisioned including toggles, rotatable and slidable knobs, pivotable levers or triggers, pistol grips, in-line handles, remotely operated systems and any combination thereof. For example, as shown in FIG. 13A, the handle assembly may include a pistol-type 200 including a tool assembly rotation knob 210, an articulation lever 212 and a body rotation knob 214. The use of an above-described tool assembly as part of a robotic system is also envisioned.

It is envisioned that utilization of a heavier gauge material for the anvil assembly alone, and preferably also for the closure member and the clamping ring provides an enhanced clamping pressure along the length of the tissue which, in turn, provides a more uniform tissue gap between the respective anvil and cartridge surfaces adjacent to and ahead of where the staples are formed through tissue. Moreover, utilizing the clamping ring for pre-clamping the tissue, i.e., clamping the tissue prior to deformation of the staples, tends to force some tissue fluid distally and radially outwardly which reduces the likelihood of hydraulically displacing of the staples during their deformation. Use of a closure member or the like which clamps as it translates along the tool member helps to compensate for the fluid flow and/or from within the tissue and/or bowing out of the distal end of the anvil and thereby maintain the desired tissue gap between the anvil and the cartridge assembly.

Figure 14:
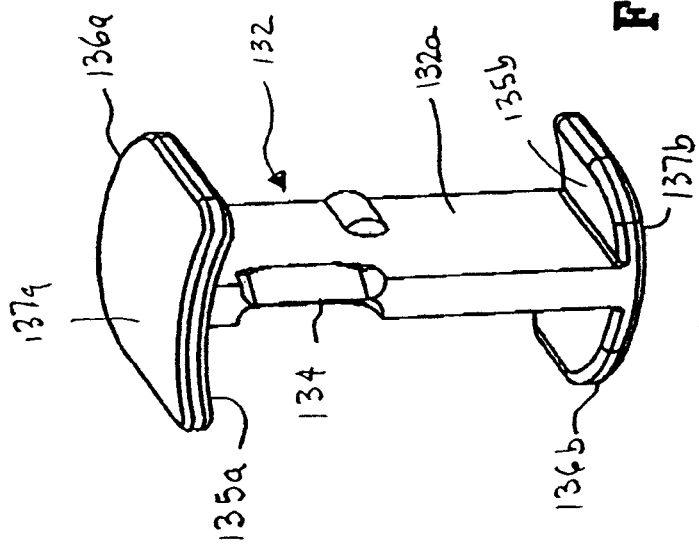
FIG. 14 is another embodiment of the closure member according to the present disclosure.

In another preferred embodiment as shown in FIG. 14, closure member 132 includes upper and lower flanges 136a, 136b spaced apart and attached to an intermediate portion 132a. As in the previous embodiment, closure member 132 is preferably positioned proximally of the sled 140 partially within a cartridge 118 of cartridge assembly 116. A knife blade 134 is preferably positioned on intermediate portion 132a of closure member 132 for incising fastened tissue. Knife blade 134 may be machined directly on a section of intermediate portion 132a or it may be fixedly or removably attached to intermediate portion 132a. Alternatively, knife blade 134 may be formed as part of sled 140 or may be fixedly or removably secured to sled 140. Upper and lower flanges 136a, 136b are generally arcuate structures with substantially identical curvatures. Alternately, the curvature of the upper and lower flanges 136a, 136b may differ to provide greater or lesser structure support. Each flange 136a, 136b further includes an inner surface 135a, 135b and an outer surface 137a, 137b. Preferably, closure member 132 is constructed so that the inner surfaces 135a, 135b are facing each other. Upper and lower flanges 136a, 136b function to define the maximum tissue gap between anvil and cartridge surfaces.

Figure 15:
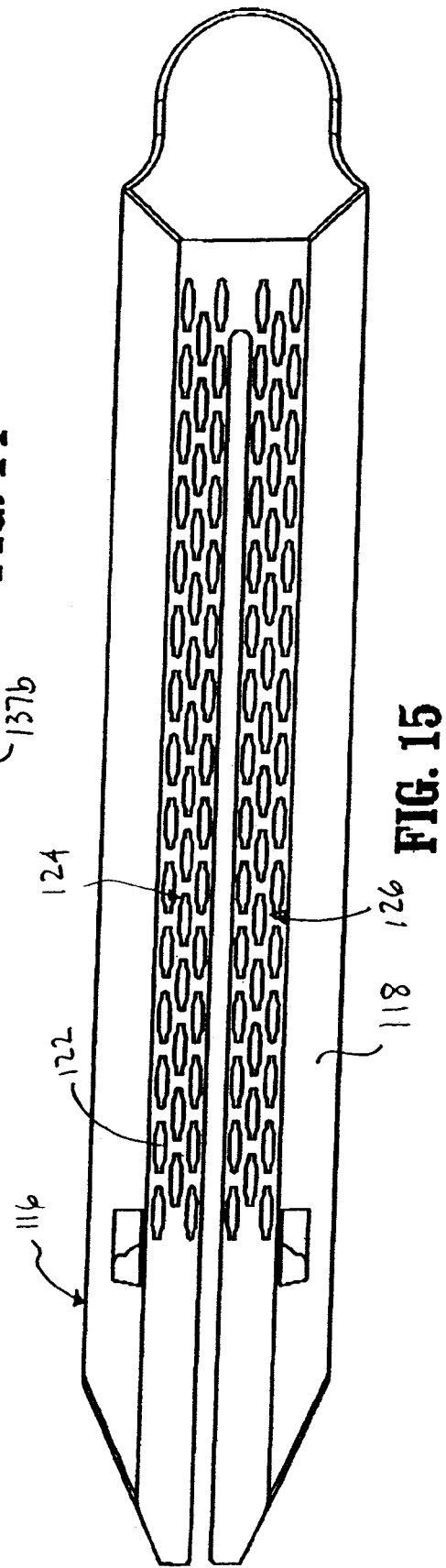
FIG. 15 is a top plan view of the cartridge housing of the present disclosure.

In one preferred embodiment, cartridge assembly 116 includes a plurality of retention slots 122 arranged along a longitudinal axis of cartridge housing 118. As shown in FIG. 15, retention slots 122 are arranged to form first and second groups 124, 126. Preferably, each group 124, 126 includes three rows of retention slots 122 configured such that at least one of the rows is longitudinally offset from the remaining rows. It is further preferred that at least two rows of retention slots 122 are disposed in each group 124, 126 of cartridge assembly 118 such that each retention slot 122 of an inner row is in substantial longitudinal alignment with a corresponding retention slot 122 in the outer row and the intermediate row of retention slots 122 is longitudinally offset from the inner and outer rows. Thusly, the inner and outer rows of retention slots 122 are longitudinally aligned from the most proximal location to the most distal location of cartridge housing 118. Preferably, a retention slot 122 in the inner and outer rows define the proximal-most and distal-most retention slot The advantageous positioning of the retention slots 122 as described improves the fastening of tissue and minimizes bleeding.

Figure 16A:
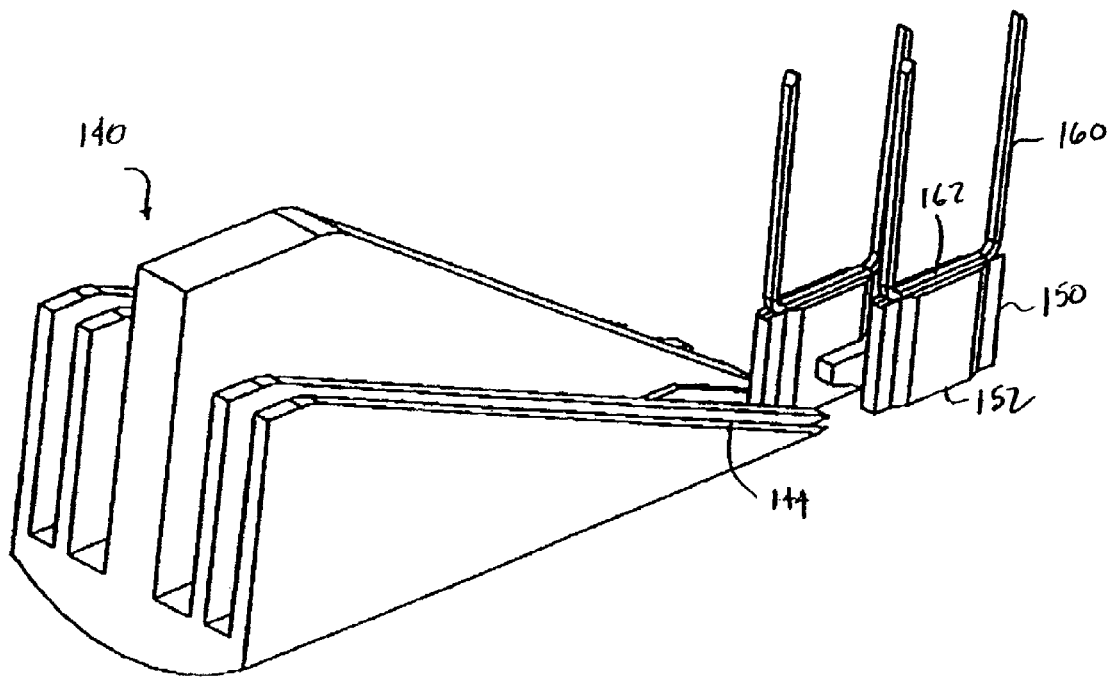
FIGS. 16A and 16B are perspective views of the sled and pusher members of the present disclosure.
Figure 16B:
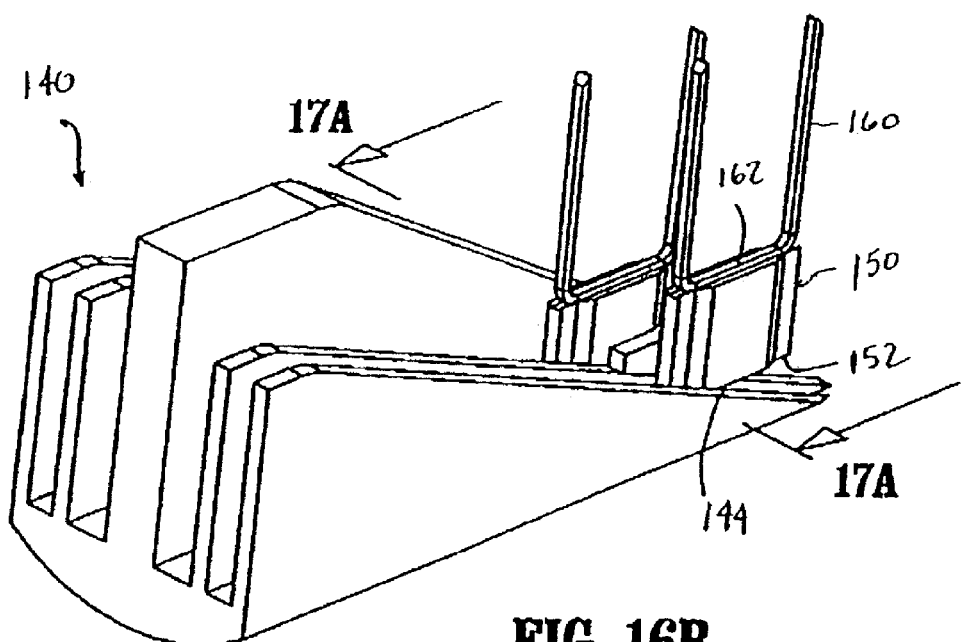
Figure 17A:
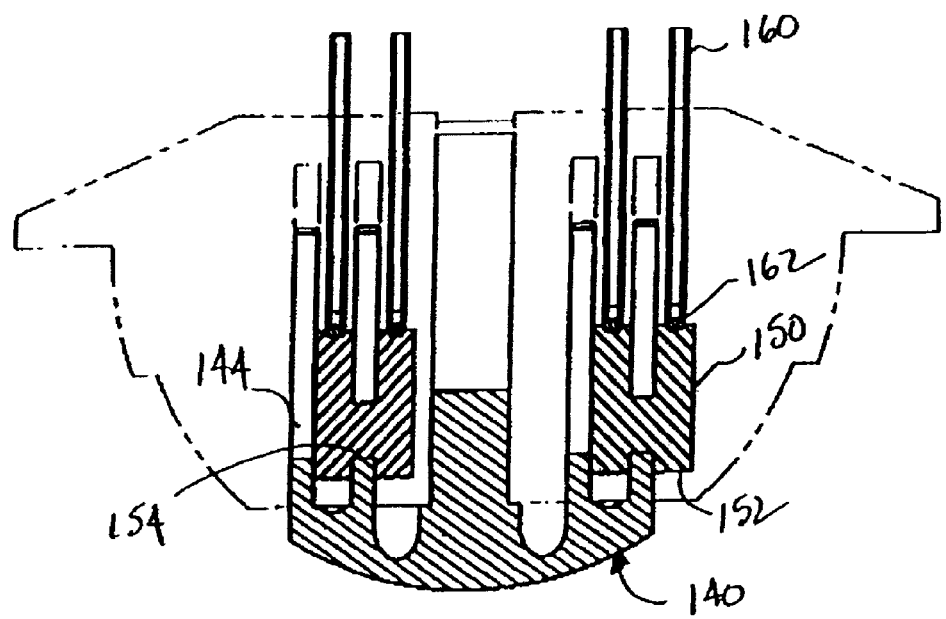
FIG. 17A is a cross-sectional end view of a portion of the cartridge assembly of FIG. 16B, taken along lines 17A, illustrating the arrangement of the sled, pusher member, and staple according to an embodiment of the present disclosure.
Figure 17B:
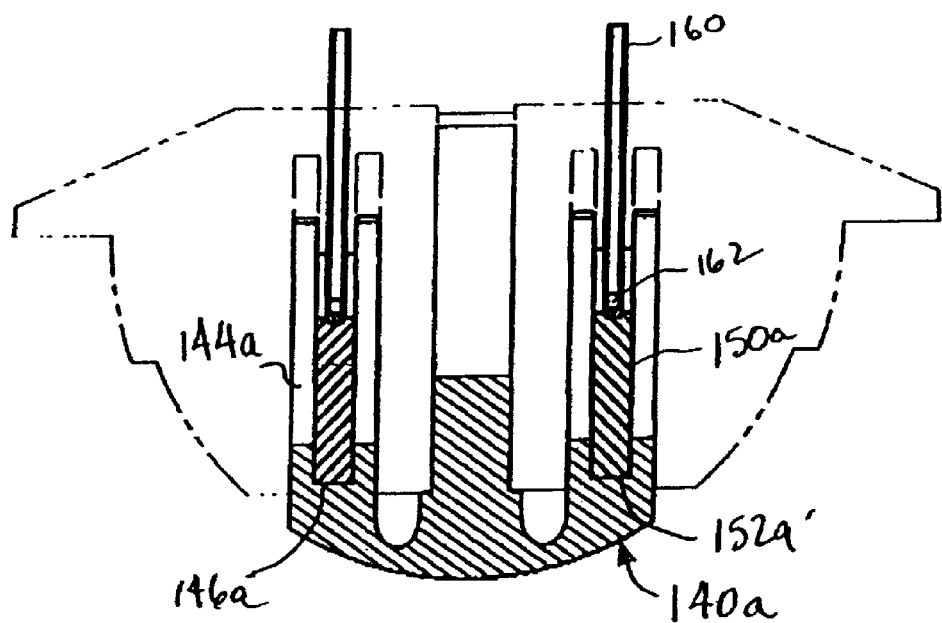
FIG. 17B is a cross-sectional end view of a portion of the cartridge assembly illustrating the arrangement of the sled, pusher member, and staple according to another embodiment of the present disclosure.

Referring to FIGS. 16A-17B, additional embodiments of sled 140 and pusher member 150 are illustrated. Pusher member 150 includes a base portion 152. In FIG. 16A, sled 140 has been advanced longitudinally in cartridge housing 118 and begins to engage base 152 of pusher member 150. As sled 140 is further advanced in a longitudinal direction (FIG. 16B), base 152 of pusher member 150 engages upstanding cam wedges 144 of sled 140. Longitudinal movement of sled 140 transfers the longitudinal motive forces along cam wedges 144 and thereby to pusher members 150. Preferably, pusher members 150 are in a fixed relationship to the longitudinal movement of sled 140 and move substantially orthogonal to the longitudinal axis of cartridge assembly 118, thereby transferring the motive forces to backspan 162 of staple 160 for moving staple 160 through retention slot 122. In one preferred embodiment, as illustrated in FIG. 17A, cam wedges 144 of sled 140 engage a recess 154 in pusher member 122. Recess 154 is configured and adapted for sliding engagement of cam wedge 144. Once cam wedge 144 engages recess 154, further longitudinal movement of sled 140 acts to maintain pusher member 150 in substantial vertical alignment to the longitudinal axis. Thusly configured, once engaged by sled 140, pusher member 150 maintains its substantially orthogonal relationship to the longitudinal axis as it moves through retention slot 122. Alternatively, pusher member 150a may be configured to reside with a space 146a between cam wedges 144a of sled 140a as shown in FIG. 17B. As in the previous embodiment, base 152a of pusher member 150a is configured and adapted for sliding engagement with space 146a of sled 140a. Further still, as pusher member 150a engages cam wedge 144a of sled 140a, pusher member 150a maintains its substantially orthogonal relationship to the longitudinal axis as it moves through retention slot 122.

It will be understood that various modifications may be made to the embodiments disclosed herein. For example, although the tool assembly is described exclusively as a stapling device, it may be used to apply fasteners other than staples including two-part fasteners. Therefore, the above description should not be construed as limiting, but merely as exemplifications of preferred embodiments. Those skilled in the art will envision other modifications within the scope and spirit of the claims appended hereto.

What is claimed is:

1. A surgical stapling device, comprising:
a tool assembly, including:
an anvil;
a cartridge assembly having a plurality of surgical staples;
a dynamic clamping member, the dynamic clamping member having an upper flange for engaging the anvil and a lower flange for engaging the cartridge assembly, the anvil and cartridge assembly being movable in relation to each other between open and clamped positions;
a sled slidably positioned to translate through the cartridge assembly to eject the staples from the cartridge assembly, the dynamic clamping member being positioned proximally of the sled in engagement therewith and translatable through the cartridge assembly;
a clamp ring movable from a retracted position to an advanced position encircling proximal portions of the anvil and cartridge assembly for preventing a gap between proximal portions of the anvil and cartridge assembly from exceeding a predetermined distance;
a drive mechanism for advancing the clamp ring and dynamic clamping member;
wherein the drive mechanism includes a flexible member attached to the dynamic clamping member and movable distally to advance the dynamic clamping member distally through the cartridge assembly and a sheath positioned about the flexible member, the sheath being connected to the clamp ring.

2. The surgical stapling device of claim 1, wherein the dynamic clamping member includes a knife blade for cutting tissue.

3. The surgical stapling device of Claim 1, wherein the dynamic clamping member includes a recess for receiving a distal end of the flexible member.

4. The surgical stapling device of claim 3, wherein the distal end of the flexible member is shaped to conform to the recess.

5. The surgical stapling device of claim 1, wherein the cartridge assembly has a cam surface and the lower flange engages the cam surface to pivot the cartridge assembly from the spaced position to the approximated position.

6. The surgical stapling device of claim 1, wherein the tool assembly is mounted for articulation about a pivot axis.

7. The surgical stapling device of claim 6, further comprising a pivot member at the pivot axis.

8. The surgical stapling device of claim 7, further comprising an articulation link attached to the tool assembly at a location offset from the pivot member.

9. The surgical stapling device of claim 8, further comprising a collar, the pivot member being connected to the collar.

10. The surgical stapling device of claim 9, wherein the anvil and cartridge assembly are rotatable in relation to the collar.

11. The surgical stapling device of claim 1, wherein the clamp ring remains positioned around the proximal end of the anvil and the proximal end of the cartridge assembly while the dynamic clamping member moves to eject the staples from the cartridge.

12. The surgical stapling device of claim 1, further comprising an endoscopic body portion, the tool assembly being supported at a distal end of the endoscopic body portion.

13. The surgical stapling device of claim 1, further comprising a handle assembly for actuating the tool assembly.

* * * * *